United States Patent [19]

Feldman

[11] E Re. 30,669

[45] Reissued Jul. 7, 1981

[54] MICROBIAL RENNIN

[75] Inventor: Louis Feldman, Spring Valley, N.Y.

[73] Assignee: Gist-Brocades N.V., Delft, Netherlands

[21] Appl. No.: 85,069

[22] Filed: Oct. 15, 1979

Related U.S. Patent Documents

Reissue of:

[64] Patent No.: 4,136,201
Issued: Jan. 23, 1979
Appl. No.: 860,636
Filed: Dec. 14, 1977

U.S. Applications:

[63] Continuation of Ser. No. 688,349, Dec. 6, 1967, abandoned, which is a continuation-in-part of Ser. No. 631,608, Apr. 18, 1967, abandoned.

[51] Int. Cl.[3] ..... C12N 9/58; A23C 19/02

[52] U.S. Cl. ..... 426/36; 435/223; 435/931

[58] Field of Search ..... 435/223; 426/42, 36

[56] References Cited

U.S. PATENT DOCUMENTS 3,988,207 10/1976 Aunstrup ..... 435/223

*Primary Examiner*—Lionel M. Shapiro
*Attorney, Agent, or Firm*—Hammond & Littell, Weissenberger and Muserlian

[57] ABSTRACT

The production of a rennin of high milk coagulating activity and low proteolytic activity from a selected strain of Mucor miehei which is useful in cheese making.

8 Claims, No Drawings

MICROBIAL RENNIN

Matter enclosed in heavy brackets [ ] appears in the original patent but forms no part of this reissue specification; matter printed in italics indicates the additions made by reissue.

This is a continuation of copending application Ser. No. 688,349 filed Dec. 6, 1967, which in turn is a continuation-in-part of co-pending Application Ser. No. 631,608, filed Apr. 18, 1967, both now abandoned.

This invention relates to a method of making a microbial rennin and to a method of making cheese with said rennin.

The conventional method of making cheese involves the use of rennet for coagulating milk. Rennet is an enzyme-containing composition prepared from the fourth stomach of milk-fed calves. In the process of making cheese, the rennet is added to milk and the enzyme, rennin, exerts a mildly proteolytic action on the casein and other proteins present in the milk. This breakdown of the proteins causes the milk to coagulate or to form solid curds. These curds are separated from the whey, which is predominantly an aqueous suspension of low solids content. The curds are then mixed with salt, etc., and formed into blocks or rounds and cured to form cheese.

Because of the particular animal origin of rennet, the supply and quality of rennet are subject to wide fluctuations. In view of these variable factors, investigators in the field have attempted to find cheese making substitutes for rennet. Numerous vegetable and microbial enzyme preparations have been investigated in the search for suitable substitute materials having the milk coagulating properties of rennet. Among the microorganisms which have been disclosed as useful for this purpose are, for example, the various microorganisms disclosed in U.S. Pat. No. 1,391,219, the Endothia parasitica disclosed in U.S. Pat. No. 3,275,453 and the Mucor pusillus disclosed in U.S. Pat. Nos. 3,151,039 and 3,212,905.

In accordance with the present invention a microbial rennin having high milk coagulating activity and low proteolytic activity is prepared by inoculating a medium containing available carbon, nitrogen and trace nutrients with a culture of a selected strain of Mucor mieher, fermenting under aerobic conditions until a substantial amount of said microbial rennin is produced, and thereafter recovering the microbial rennin from the fermentation medium. The rennin thus prepared can be used in the process of making cheese during the milk coagulating step as a substitute for part or all of the rennet normally used.

A description of the general characteristics of the organism Mucor miehei is provided by Cooney and Emerson, "Thermophilic Fungi," pp. 17-27 (1964), published by W. H. Freeman and Co., San Francisco and London. NRRL.

Cultures of the selected strains of Mucor miehei used in accordance with the present invention are on deposit with the Northern Regional Research Laboratories, Peoria, Ill., and available to the public under the code designation NRRL 3169, NRRL A7772, NRRL A13131, NRRL A13042 and ANRRL 2543. By way of distinction, it has been found that another strain of Mucor miehei, available from the above laboratories under the code designation NRRL A6588, has essentially no capacity to produce a microbial rennin as herein described. The preferred strains of Mucor miehei are those designated NRRL 3169, NRRL A7772, NRRL A13131 and NRRL A13042.

The microbial rennin of the present invention preferably is prepared by growing a culture of a selected strain of Mucor miehei in a suitable medium in the presence of air at temperatures of from about 30° C. to about 55° C. for periods of time of from about 2 to about 14 days. The fermentation medium generally has a pH of from about 3 to about 8 and preferably a pH of from about 4 to about 7. Submerged aerobic fermentation methods, for example, deep fermentation in commercial fermentation tanks or fermentation in flasks on a rotary shaker, as well as various methods of surface aerobic fermentation can be used to prepare the microbial rennin of the present invention.

Recovery of the microbial rennin from the filtered fermentation medium can be carried out by various methods conventionally used in the separation of proteins from mixtures, for example, solvent precipitation, salt precipitation, chromatography and other such methods of protein recovery. Examples of solvents that can be used for the precipitation of the microbial rennin are ketones such as acetone and methyl ethyl ketone, alcohols such as methanol, ethanol and isopropanol, and other such organic solvents. Illustrative of the salts which can be employed are ammonium sulfate, sodium sulfate and the like mineral salts. Still other methods of recovery of the microbial rennin can be used, for example, dialysis, electrophoresis, freeze-drying and the like.

Suitable fermentation media can be prepared from carbohydrate materials such as whey, degraded corn starch, Cerelose, wheat bran and other organic sources of available carbon, and from nitrogenous materials such as brewers' yeast, soya protein, casein, urea, ammonium salts, nitrates and other such organic or inorganic sources of available nitrogen. The sources of these fermentation media ingredients may be crude natural materials or more highly purified substances. Trace nutrients that may be required by the organism are usually present with the major fermentation media ingredients, such that the separate addition of trace nutrients is generally not required. For example, trace amounts of inorganic salts such as metal chlorides, sulfates, phosphates and nitrates are generally present in the fermentation media in association with the carbonaceous and nitrogenous ingredients.

Proteases, in general, coagulate milk. However, most proteases cause considerable protein digestion. When these proteases, of animal, plant and microbial origin, are employed for the coagulation of milk, the resulting curds develop undesirable off-flavors due to proteolysis and thus are not well suited for cheese making. A principal advantage of the present invention is that the rennin prepared from Mucor miehei as herein described unexpectedly has a very low proteolytic activity associated with high milk coagulating activity. The milk proteolysis curves obtained with the Mucor miehei of the present invention are identical to those obtained with rennet, which indicates a very low proteolytic activity. The Mucor miehei rennin also appears to be substantially less proteolytic than the Mucor pusillus disclosed in U.S. Pat. No. 3,151,039. Using the Mucor miehei rennin, less than 10% of the total Kjeldahl nitrogen has been found in whey whereas 20% Kjeldahl nitrogen transfers into the whey according to U.S. Pat. No. 3,151,039 (column 4, lines 58-61).

Although the inventor is not to be bound by any particular theory, it is believed that the cheeses made with the microbial rennin of the present invention are essentially free from any off-flavors due in a large measure to the low proteolytic activity in the rennin product.

In the production of certain cheeses it is desirable to use a microbial rennin obtained from Mucor miehei in which the rennin is essentially free from any lipase whereas in the production of certain other cheeses it may be desirable to use a microbial rennin obtained from Mucor miehei in which the rennin contains lipase. It will be understood that both of the aforesaid microbial rennins are included within the scope of the present invention.

The following examples will further illustrate the present invention although the invention is not limited to these specific examples. All percentages expressed herein are on a weight basis unless otherwise specified.

EXAMPLE 1

Mucor miehei, NRRL 3169, is transferred from an agar slant under sterile conditions into a one liter Fernbach flask containing 200 ml of the following aqueous medium:

| | |
|---|---|
| Whey | 82% |
| Degraded corn starch | 5% |
| Brewers' yeast | 1% |
| Cerelose (glucose) | 1% |
| Water | 11% |
| | 100% |

The flask is incubated on a rotary shaker at 37° C. for 168 hours. The fermentation broth is filtered and the filtrate shows an activity equal to 12,680 mcg NF rennet/ml. To the chilled filtrate (<5° C.) is added two volumes of cold acetone. The resulting precipitate is filtered and washed with acetone, yielding a fine white powder with an activity of 968 mg NF rennet/g.

The activity of rennin containing material as described herein is determined in the following manner: To 9 ml of fresh homogenized milk (pH adjusted to 6.2 with lactic acid) at 35° C. is added one ml of aqueous solution of rennin sample. The sample is agitated periodically and the time required for the first appearance of flocculation is observed. The same procedure is conducted simultaneously using several levels of NF rennet. A standard curve is prepared for flocculation time versus level of NF rennet. The flocculation time for the test sample is then related to the standard curve to determine the activity of the test sample in terms of NF rennet.

The microbial rennin product prepared in the above example can be used as a substitute for part or all of the rennet normally used in the making of ripened cheeses such as, for example, Cheddar type cheeses, Swiss cheese and other such so-called hard and soft cheeses, and for any other types of cheeses wherein rennet preparations have heretofore been used.

EXAMPLE 2

The procedure of Example 1 is repeated, substituting for Mucor miehei, NRRL 3169, the strain of Mucor miehei designated NRRL 2543 by the Northern Regional Research Laboratories. Rennin activity for the production of a satisfactory cheese is obtained.

EXAMPLE 3

The procedure of Example 1 is repeated, substituting for the aqueous fermentation medium, the following media:

| | | |
|---|---|---|
| (a) | Whey | 97% |
| | Glucose | 3% |
| | | 100% |
| (b) | Degraded corn starch | 5% |
| | Brewers'yeast | 1% |
| | Cerelose (glucose) | 1% |
| | Whey | 0-80% |
| | Water | 13-93% |
| | | 100% |
| (c) | Whey | 50% |
| | Degraded corn starch | 5% |
| | Cerelose (glucose) | 1% |
| | Nitrogen source* | 0.5-5% |
| | Water | 39-43.5% |
| | | 100% |

*Casein, soya protein, peptone, enzymatically degraded casein, or corn steep liquor.

The above fermentation media are further examples of suitable media containing available carbon, nitrogen and trace nutrients for the preparation of a microbial rennin of relatively high milk coagulating activity and relatively low proteolytic activity in accordance with the procedure described herein.

EXAMPLE 4

In place of the submerged fermentation in liquid media of Example 1, Mucor miehei rennin is prepared in (a) still and (b) agitated fermentations on semi-solid media comprising 25% wheat, 25% sugar beet pulp and 50% whey. These rennin products can be used to prepare satisfactory hard and soft cheeses.

EXAMPLE 5

A Cheddar cheese is made by substituting for the rennet preparation ordinarily used in the setting step, an equivalent amount of the microbial rennin product prepared in Example 1. In this procedure, pasteurized whole milk is adjusted to 86°-88° F. and one percent by weight of a commercial lactic acid starter solution is added. The microbial rennin is then added to the milk at a rate of 3 ounces per 1000 pounds of milk. The mixture is agitated until a curd of satisfactory firmness is obtained. The curd is cut into cubes and then cooked at 100° F. for several hours. The curd is separated from the whey and layered into slabs. The milled curd is then salted with 3% by weight of cheese salt. The salted curd is transferred to hoops, pressed, and then placed in a curing room. The cheese made from the microbial rennin of this example is sampled periodically after several days of curing and is found to possess excellent qualities and to be essentially free from off-flavors.

Other conventional methods of making Cheddar cheese, for example, those generally described by Prescott and Dunn, "Industrial Microbiology", Chapter 21 (3d ed. 1959), McGraw-Hill Book Co., Inc., New York, and references cited therein, can be used in the practice of the present invention by substitution for the rennet preparations ordinarily employed in said cheese making, an equivalent amount of the microbial rennin from Mucor miehei of Example 1 herein, to produce good quality cheese.

EXAMPLE 6

In order to demonstrate the importance of the use of a selected strain of Mucor miehei, Example 1 was repeated up to the point of filtration of the fermentation broth except that the following strains were each substituted for the strain designated NRRL 3169:

NRRL A7772,
NRRL A13042,
NRRL A13131,
NRRL A6588, and incubation was carried out for up to 258 hours. Samples of the fermentation broth were withdrawn periodically during the incubation and product recovered and assayed for rennet activity as in Example 1. The following Table A sets forth the rennet activity determined for these samples.

| Incubation Time (hours) | Activity (mcg NF rennet/ml.) NRRL A6588 | NRRL A7772 | NRRL A13042 | NRRL A13131 |
|---|---|---|---|---|
| 90 | 120 | 6,420 | 5,100 | 4,380 |
| 115 | 90 | 7,400 | 5,750 | 5,200 |
| 138 | 90 | 8,200 | 5,750 | 5,560 |
| 162 | * | 8,700 | 5,150 | 5,430 |
| 186 | * | 9,100 | 5,300 | 6,000 |
| 258 | * | 10,100 | 4,670 | 9,360 |

* Incubation discontinued after 138 hours

From the above demonstration it is evident that the capacity to produce microbial rennin varies among different strains of Mucor miehei and that the strain designated A6588 has virtually no capacity to produce microbial rennin.

EXAMPLE 7

Examples 1 and 2 were repeated up to the point of filtration of the fermentation broth except that the temperature of incubation was 30° C., the aqueous fermentation medium consisted of 97% whey and 3% glucose, and incubation was carried out for up to 282 hours. Samples of the fermentation broth were withdrawn periodically during the incubation and product recovered and assayed for rennet activity as in Example 1. The following Table B sets forth the rennet activity determined for these samples.

TABLE B

| Incubation Time (hours) | Activity (mcg NF rennet/ml.) NRRL 2543 | NRRL 3169 |
|---|---|---|
| 114 | 80 | 228 |
| 138 | 112 | 460 |
| 162 | 143 | 605 |
| 186 | 211 | 1,140 |
| 210 | 248 | 1,470 |
| 282 | 333 | 1,800 |

From the above comparison it can be seen that the strain of Mucor miehei designated NRRL 2543 has the ability to produce a microbial rennin but it is not as great as that of the strain designated NRRL 3169 which is a preferred strain.

EXAMPLE 8

In order to demonstrate the production of microbial rennins from the selected strains of Mucor miehei defined herein both with and without the formation of lipase, the following procedure was carried out:

Fermentations were conducted, employing the strains of Mucor miehei designated NRRL A7772 and NRRL 3169, in ten liter stirred, aerated glass fermentors at 37° C. for 168 hours. The media employed and the rennin activity of the filtrate of the fermentation broth is set forth in Table C, below.

TABLE C

| Fermentation No. | | 1 | 2 | 3 |
|---|---|---|---|---|
| M. miehei strain | | A7772 | 3169 | 3169 |
| Medium: | Whey | 50% | 50% | 80% |
| | Degraded corn starch | 5 | 5 | 5 |
| Fermentation No. | | 1 | 2 | 3 |
| M. miehei strain | | A7772 | 3169 | 3169 |
| | Brewer's yeast | 1 | 1 | 1 |
| | Cerelose (glucose) | 1 | 1 | 1 |
| | Water | 43 | 43 | 13 |
| | | 100% | 100% | 100% |
| Filtrate: | Rennin activity mcg NF rennet/ml | 4,380 | 8,650 | 9,000 |

The filtrates of the fermentation broths in fermentation numbers 1, 2 and 3, above, were then treated as follows:

Fermentation No. 1: Added two volumes of acetone to the filtrate to yield a white precipitate having the following activities:
Rennin: 460 mg NF rennet/g.
Lipase: 0 units/g.

Fermentation No. 2: Added two volumes of acetone to the filtrate to yield a precipitate having the following activities:
Rennin: 540 mg NF rennet/g.
Lipase: 38 units/g.

Fermentation No. 3: To each 100 ml. of filtrate was added 3.0 grams of $CaCl_2$ and 500 ml. ethanol to yield a tan precipitate having the following activities:
Rennin: 652 mg NF rennet/g.
Lipase: 0 units/g.

The rennin activity is defined as hereinbefore and the lipase unit is defined as that quantity of enzyme (lipase) which produces one micro-equivalent of acid per minute at pH 6.5 at 30° C. from an olive oil substrate.

As will be readily apparent to those skilled in the art, other examples of the herein-defined invention can be devised after reading the foregoing specification and claims appended hereto by various modifications and adaptations without departing from the spirit and scope of the invention as defined in the following claims.

What is claimed is:

1. A microbial rennin having relatively high milk coagulating activity and relatively low proteolytic activity and being [relatively] *substantially* free from lipase obtained by cultivating a selected strain of Mucor miehei [(NRRL No's: 3169, A7772, A13131, A13042, and 2543)] *capable of producing microbial rennin* in a medium containing available carbon, nitrogen and trace nutrients and fermenting under aerobic conditions.

2. The process of preparing a lipase-free rennin with a relatively high milk coagulating activity and relatively low proteolytic activity comprising fermenting under aerobic conditions a medium containing available carbon, nitrogen and trace nutrients and at least one Mucor miehei strain [selected from the group consisting of NRRL No. 3169, No. A7772, A13131 and A13042] *capable of producing microbial rennin* until a substantial amount of microbial rennin is produced and recovering a lipase-free rennin from the resulting fermentation medium.

3. The process of claim 2 in which the fermentation is carried out under submerged aerobic conditions at a temperature of from about 30° C. to about 55° C. for about 2 days to about 14 days.

4. In the process of making cheese including the step of preparing curds from milk, the improvement comprising substituting for at least part of the rennet normally used in the said step the lipase-free microbial rennin of claim 1.

5. The process of claim [4] *2* wherein the Mucor miehei strain is NRRL No. A-13042.

6. The rennin of claim 1 wherein the Mucor miehei strain is NRRL No. A-13042.

*7. A microbial rennin of claim 1 wherein the Mucor miehei strain is selected from the group consisting of NRRL No. 3169, A7772, A13131 and A13042.*

*8. The process of claim 2 wherein the Mucor miehei strain is selected from the group consisting of NRRL No. 3169, A7772, A13131 and A13042.*

* * * * *

UNITED STATES PATENT AND TRADEMARK OFFICE

CERTIFICATE OF CORRECTION

PATENT NO. : RE 30,669

DATED : July 7, 1981

INVENTOR(S) : Louis Feldman

It is certified that error appears in the above—identified patent and that said Letters Patent is hereby corrected as shown below:

On The Title Page item

[73] "Gist-Brocades N.V., Delft, Netherlands" should be

--GB Fermentation Industries, Inc. Kingstree, S.C.--

Signed and Sealed this

*Eleventh* Day of *May 1982*

[SEAL]

*Attest:*

GERALD J. MOSSINGHOFF

*Attesting Officer*

*Commissioner of Patents and Trademarks*